United States Patent
Washer et al.

(10) Patent No.: US 11,782,005 B2
(45) Date of Patent: Oct. 10, 2023

(54) VOLATILE ALKENE SENSING DEVICE AND METHOD OF USING

(71) Applicant: Carrier Corporation, Palm Beach Gardens, FL (US)

(72) Inventors: Benjamin M. Washer, West Lafayette, IN (US); Aiganym Yermembetova, West Lafayette, IN (US); Alexander Wei, West Lafayette, IN (US)

(73) Assignee: Carrier Corporation, Palm Beach Gardens, FL (US)

( * ) Notice: Subject to any disclaimer, the term of this patent is extended or adjusted under 35 U.S.C. 154(b) by 124 days.

(21) Appl. No.: 17/118,242

(22) Filed: Dec. 10, 2020

(65) Prior Publication Data

US 2021/0262961 A1   Aug. 26, 2021

Related U.S. Application Data

(60) Provisional application No. 62/981,239, filed on Feb. 25, 2020.

(51) Int. Cl.
| | |
|---|---|
| *G01N 27/04* | (2006.01) |
| *G01N 1/40* | (2006.01) |
| *B82Y 15/00* | (2011.01) |
| *B82Y 30/00* | (2011.01) |

(52) U.S. Cl.
CPC ............ *G01N 27/04* (2013.01); *G01N 1/405* (2013.01); *B82Y 15/00* (2013.01); *B82Y 30/00* (2013.01)

(58) Field of Classification Search
CPC ...... G01N 27/04; G01N 1/405; G01N 27/127; G01N 33/0011; G01N 33/0047; B82Y 15/00; B82Y 30/00
See application file for complete search history.

(56) References Cited

U.S. PATENT DOCUMENTS

| | | | |
|---|---|---|---|
| 4,999,034 A | 3/1991 | Mager et al. | |
| 6,703,241 B1 | 3/2004 | Sunshine et al. | |
| 7,320,725 B2 * | 1/2008 | Arno | B01D 53/261 96/138 |
| 9,964,511 B2 * | 5/2018 | Sommer | G01N 27/36 |

(Continued)

FOREIGN PATENT DOCUMENTS

| | | | |
|---|---|---|---|
| CN | 207946118 U | * | 10/2018 |
| DE | 4028062 A1 | | 3/1992 |

(Continued)

OTHER PUBLICATIONS

Lee et al., "Two-Dimensional Transition Metal Dichalcogenides and Metal Oxide Hybrids for Gas Sensing", ACS Sens. 2018, 3, 2045-2060 (Year: 2018).*

(Continued)

*Primary Examiner* — Alexander Satanovsky
*Assistant Examiner* — Asm Fakhruddin

(57) ABSTRACT

A volatile alkene sensing device includes a gas pathway having a desiccant area located upstream of a sensor, wherein the sensor is disposed in a housing. The sensor includes a conductive region in electrical communication with two electrodes. The conductive region includes nano-sized particles of a metal dichalcogenide, a mercaptoimidazolyl metal-ligand complex, and single-walled carbon nanotubes or metallic nanowires.

20 Claims, 3 Drawing Sheets

(56) References Cited

U.S. PATENT DOCUMENTS

| | | | |
|---|---|---|---|
| 2013/0273665 A1* | 10/2013 | Swager | G01N 33/0047 422/90 |
| 2016/0018338 A1 | 1/2016 | Song et al. | |
| 2017/0160005 A1 | 6/2017 | Park et al. | |
| 2017/0212069 A1 | 7/2017 | Nakao et al. | |
| 2018/0052083 A1 | 2/2018 | Murashima et al. | |
| 2018/0149565 A1 | 5/2018 | Nakao et al. | |
| 2018/0252624 A1* | 9/2018 | Oka | G01N 1/2214 |
| 2019/0170619 A1* | 6/2019 | Nakao | G01N 1/405 |

FOREIGN PATENT DOCUMENTS

| | | | | |
|---|---|---|---|---|
| JP | H11148907 A | 6/1999 | | |
| JP | 3834915 B2 | 10/2006 | | |
| JP | 4154274 B2 * | 9/2008 | | G01N 21/27 |
| JP | 2018072168 A | 5/2015 | | |
| WO | 2019151129 A1 | 8/2019 | | |
| WO | 2019226955 A1 | 11/2019 | | |

OTHER PUBLICATIONS

Esser et al., "Selective Detection of Ethylene Gas Using Carbon Nanotube-basedDevices: Utility in Determination of Fruit Ripeness", Angew. Chem. Int. Ed.2012,51, 5752-5756, (Year: 2012).*

Chen et al., "Selective Detection of Ethylene by MoS2—Carbon Nanotube Networks Coated with Cu(I)—Pincer Complexes", ACS Sensors, 2020, 5, 8 pages.

Esser et al., "Selective Detection of Ethylene Gas Using Carbon Nanotube-based Devices: Utility in Determination of Fruit Ripeness", Angew. Chem. Int. Ed., 2012, 51, pp. 5752-5756.

European Search Report for European Application No. 20212549.8; Application Filing Date: Dec. 8, 2020; dated May 28, 2021; 5 pages.

Fu et al., "Ultrasensitive Ethene Detector Based on a Graphene-Copper(I) Hybrid Material", Nano Letters, 2017, 17, 9 pages.

Ping et al., "Recent Advances in Sensing Applications of Two-Dimensional Transition Metal Dichalcogenide Nanosheets and Their Composites", Advanced Functional Materials, 2017, 27, 18 pages.

* cited by examiner

VOLATILE ALKENE SENSING DEVICE AND METHOD OF USING

CROSS-REFERENCE TO RELATED APPLICATIONS

This application claims the benefit of U.S. Provisional Application No. 62/981,239, filed Feb. 25, 2020, the disclosure of which is incorporated herein by reference in its entirety.

BACKGROUND

Exemplary embodiments pertain to the art of sensor compositions based on metal-ligand complexes.

Volatile compounds with a double bond form an important group of compounds for detection. In particular, volatile alkenes, such as ethylene, are analytes of considerable importance. In particular, the detection of ethylene is important to industries related to produce and agriculture. Due to its small size and limited chemical functionality, however, ethylene is a challenging chemical analyte to detect. More efficient and sensitive methods of detection than those currently available are desired.

BRIEF DESCRIPTION

Disclosed is a volatile alkene sensing device including a gas pathway having a desiccant area located upstream of a sensor, wherein the sensor is disposed in a housing. The sensor includes a conductive region in electrical communication with two electrodes. The conductive region includes nanosized particles of a metal dichalcogenide, a mercaptoimidazolyl metal-ligand complex, and single-walled carbon nanotubes or metallic nanowires.

In addition to one or more of the features described above, or as an alternative to any of the foregoing embodiments, the desiccant area comprises a desiccant material.

In addition to one or more of the features described above, or as an alternative to any of the foregoing embodiments, the desiccant area is a removable cartridge.

In addition to one or more of the features described above, or as an alternative to any of the foregoing embodiments, the sensor is connected to a control module.

In addition to one or more of the features described above, or as an alternative to any of the foregoing embodiments, the volatile alkene sensing device further includes a suction device, pressure feeder or both.

In addition to one or more of the features described above, or as an alternative to any of the foregoing embodiments, the nanosized particles of a metal dichalcogenide comprise $MoS_2$, $WS_2$, $MoSe_2$, $WSe_2$, $MoTe_2$, $WTe_2$, and combinations thereof.

In addition to one or more of the features described above, or as an alternative to any of the foregoing embodiments, the mercaptoimidazolyl metal-ligand complex comprises a homoleptic ligand with three mercaptoimidazolyl groups.

In addition to one or more of the features described above, or as an alternative to any of the foregoing embodiments, the mercaptoimidazolyl metal-ligand complex comprises Cu(I), Ag(I), or Au(I).

In addition to one or more of the features described above, or as an alternative to any of the foregoing embodiments, the mercaptoimidazolyl metal-ligand complex is a homoleptic complex of formula (II):

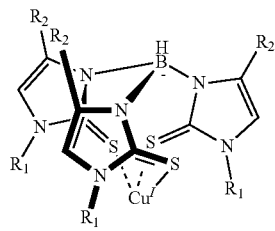

(II)

where each instance of $R_1$ and $R_2$ can be hydrogen, or a group having up to twenty carbons.

Also disclosed is a method of sensing a volatile alkene including contacting a gaseous sample with a desiccant material to form a treated sample having less than 20% relative humidity, exposing a sensor to the treated sample, and measuring an electrical property of the sensor after exposure to the treated sample. The sensor includes a conductive region in electrical communication with two electrodes. The conductive region includes nanosized particles of a metal dichalcogenide, a mercaptoimidazolyl metal-ligand complex and single-walled carbon nanotubes or metallic nanowires.

In addition to one or more of the features described above, or as an alternative to any of the foregoing embodiments, the desiccant material comprises $CaSO_4$, $Al_2O_3$, soda lime, and combinations thereof.

In addition to one or more of the features described above, or as an alternative to any of the foregoing embodiments, the treated sample has less than 10% relative humidity.

In addition to one or more of the features described above, or as an alternative to any of the foregoing embodiments, the electrical property is conductivity or resistivity.

In addition to one or more of the features described above, or as an alternative to any of the foregoing embodiments, the method further includes comparing an electrical property value obtained by measuring to a calibration curve to determine the quantity of a volatile compound having a double or triple bond present in the sample.

In addition to one or more of the features described above, or as an alternative to any of the foregoing embodiments, the volatile alkene is ethylene.

In addition to one or more of the features described above, or as an alternative to any of the foregoing embodiments, the nanosized particles of a metal dichalcogenide comprise $MoS_2$, $WS_2$, $MoSe_2$, $WSe_2$, $MoTe_2$, $WTe_2$, and combinations thereof.

In addition to one or more of the features described above, or as an alternative to any of the foregoing embodiments, the mercaptoimidazolyl metal-ligand complex comprises three mercaptoimidazolyl groups.

In addition to one or more of the features described above, or as an alternative to any of the foregoing embodiments, the mercaptoimidazolyl metal-ligand complex comprises Cu(I), Ag(I), or Au(I).

In addition to one or more of the features described above, or as an alternative to any of the foregoing embodiments, the mercaptoimidazolyl metal-ligand complex is a complex of formula (II):

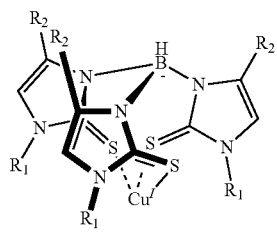

(II)

where each instance of $R_1$ and $R_2$ can be hydrogen, or a group having one or more carbons.

BRIEF DESCRIPTION OF THE DRAWINGS

The following descriptions should not be considered limiting in any way. With reference to the accompanying drawings, like elements are numbered alike.

DETAILED DESCRIPTION

A detailed description of one or more embodiments of the disclosed apparatus and method are presented herein by way of exemplification and not limitation with reference to the Figure.

Volatile compounds with double or triple bonds are a group of important compounds for detecting and monitoring. The term volatile, as used herein, refers to compounds that are in the gas phase at standard temperature and pressure. Exemplary compounds include $NO_2$, $CO_2$, $CO$, and alkenes such as $C_2H_4$ (ethylene). As the hormone responsible for initiating the ripening of fruit as well as other processes in plant development, ethylene is an analyte of considerable importance to industries related to produce and agriculture. Due to its small size and limited chemical functionality, ethylene and other volatile alkenes are challenging chemicals to detect. Disclosed herein is a volatile alkene sensing device and a method that is capable of detecting volatile alkenes such as ethylene at levels down to 100 parts per billion (ppb).

Figure 1:
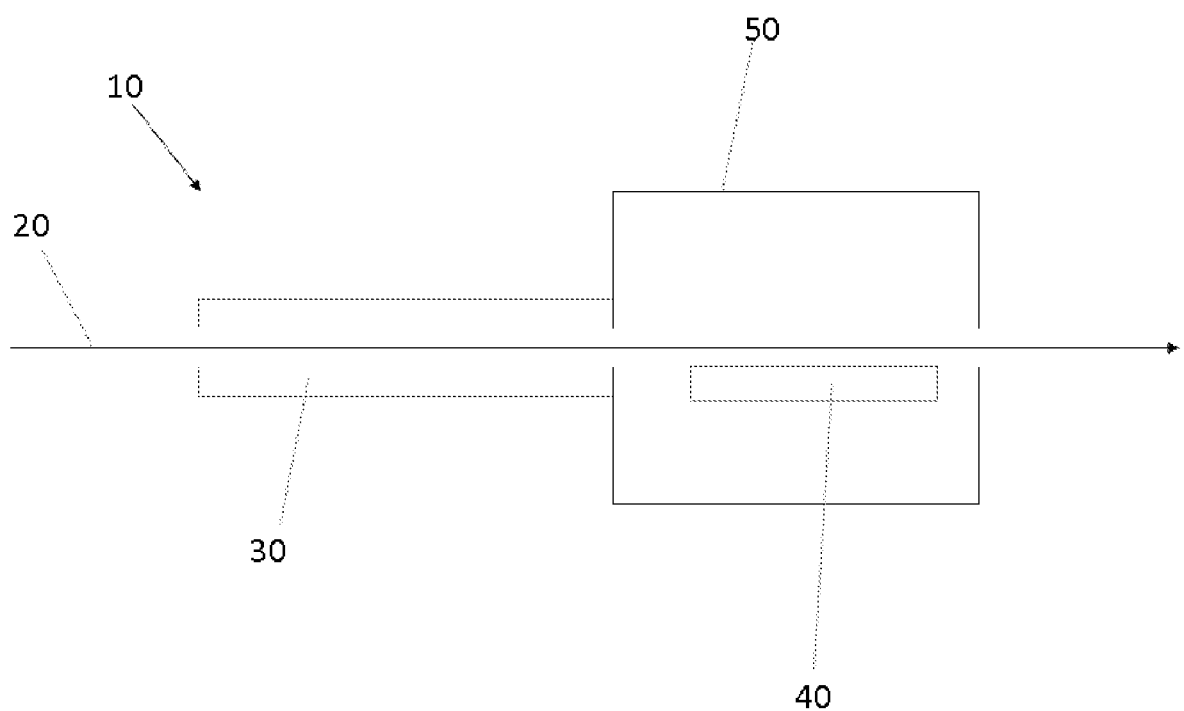
FIG. 1 is a schematic view of a volatile alkene sensing device.

As shown in FIG. 1 the volatile alkene sensing device 10 includes a desiccant area 30 disposed around a gas flow path 20 and located upstream of the sensor 40. The sensor 40 is located in a housing 50.

The desiccant area includes one or more desiccant materials (adsorbents) which are capable of adsorbing water but do not adsorb the volatile alkene in any detectable amount. Exemplary desiccant materials include $CaSO_4$, $Al_2O_3$, soda lime ($CaO/Ca(OH)_2$) and combinations thereof. The desiccant area may be in the form of a removable cartridge which can be replaced. It is also contemplated that the desiccant in the cartridge can be regenerated or replaced with new desiccant material. The amount of the desiccant can vary depending, at least in part, on aspects of the gaseous samples such as the amount of water present in the sample as well as the ability of the desiccant to remove the water.

Figure 2:
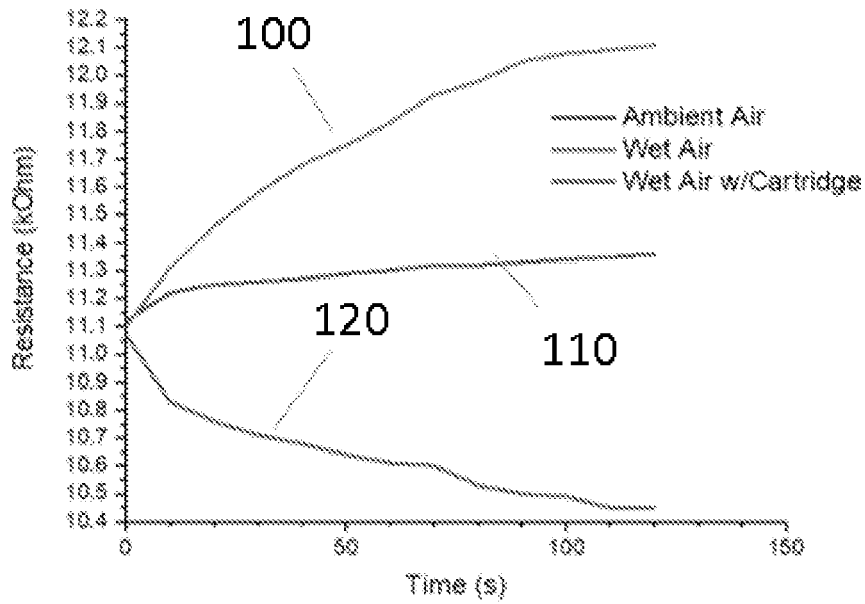
FIG. 2 is a graph of the electrode signal after exposure to air samples having differing water content.

The use of a desiccant removes interference from water when determining the presence or amount of the volatile alkene in the gaseous sample. As shown in FIG. 2, the presence of water can interfere with detecting and measuring the volatile alkene. The presence of humidity in an amount greater than 20% relative humidity can interfere with the detection and measurement of a volatile alkene such as ethylene. FIG. 2 shows the resistance of a sensor as described herein when exposed to ambient air (20% relative humidity) over time 110, when exposed to an air sample having a relative humidity level of 40% over time 100, and when exposed to an air sample having an initial relative humidity level of 40% before treatment with a desiccant 120. The electrode exposed to the air sample treated with a desiccant shows a gradual decrease in resistivity of the sample, which indicates decreasing interference from humidity due to its removal from the gas stream prior to entering the housing.

Figure 3:
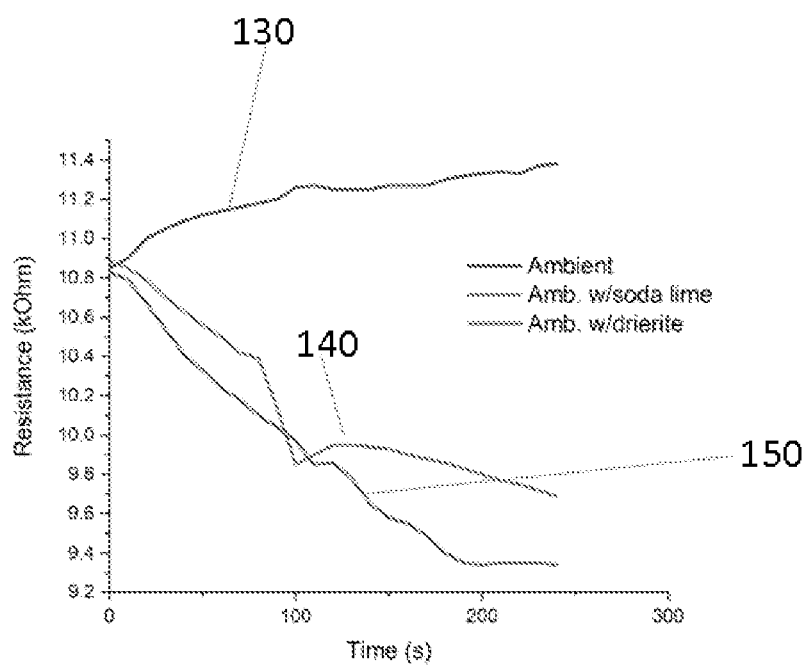
FIG. 3 is a graph of the electrode signal after exposure to air samples after treatment with different desiccants and FIG. 4 shows formula (I) for the mercaptoimidazolyl metal-ligand complex.

The use of a desiccant can also be used to remove gaseous carbon dioxide, which may also affect sensor performance depending on the relative humidity. FIG. 3 shows the resistance of a sensor as described herein when exposed to ambient air (20% relative humidity, 0.04% carbon dioxide) over time 130, when exposed to ambient air and treated with soda lime over time 140, and when exposed to ambient air and treated with $CaSO_4$ 150. The electrodes exposed to the air treated with either desiccant (soda lime or $CaSO_4$) were again successful in producing lower resistance over time.

The sensor includes a conductive region composed of nanosized particles of a metal dichalcogenide, a mercaptoimidazolyl metal-ligand complex, and single-walled carbon nanotubes or metallic nanowires.

Metal dichalcogenides include transition metal dichalcogenides which are compounds formed from a Group 6B metal and a chalcogenide (S, Se, and Te). Exemplary metal dichalcogenides include $MoS_2$, $WS_2$, $MoSe_2$, $WSe_2$, $MoTe_2$, $WTe_2$, and combinations thereof. The metal dichalcogenide is in the form of nanosized particles. "Nanosized" as it applies to the metal dichalcogenides refers to the fact that the material has at least one linear dimension of less than or equal to 100 nanometers. The metal dichalcogenides are typically available in a flake form with a thickness of 100 nanometers or less although other physical forms are not excluded such as few-layer or single-layer materials, with the caveat that the physical form has at least one linear dimension that is less than or equal to 100 nanometers.

Figure 4:
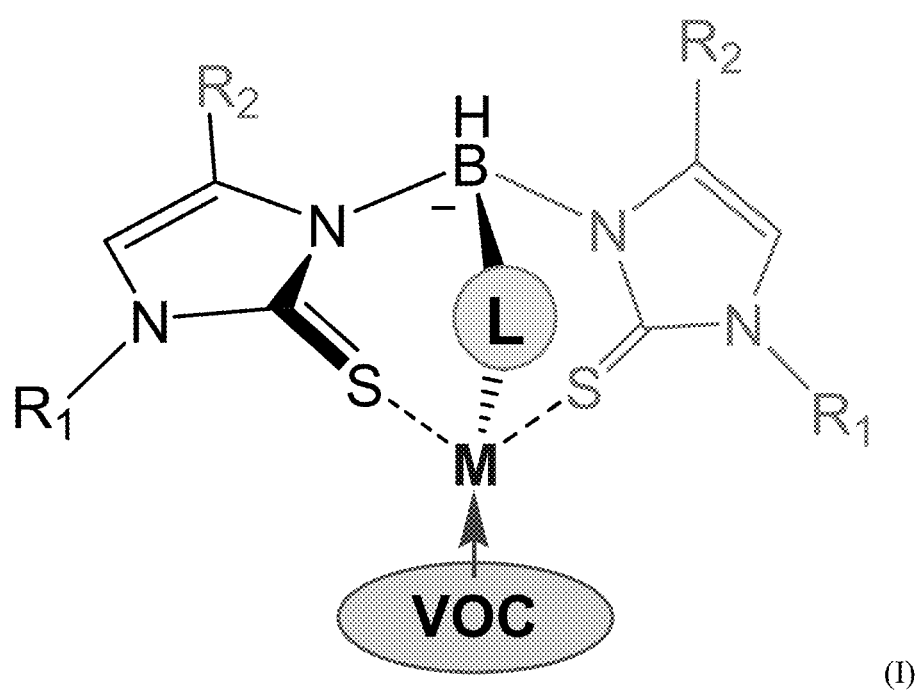

The mercaptoimidazolyl metal-ligand complex is a multidentate coordination complex comprising one or more mercaptoimidazolyl groups. The arms of the multidentate ligand (groups on the boron atom) can be the same (homoleptic) or different (heteroleptic). For example, one arm can comprise a mercaptoimidazolyl group and a second arm can comprise a pyrazolyl or indolyl group. It is also contemplated that a multidentate ligand may comprise more than one mercaptoimidazolyl group or a combination of mercaptoimidazolyl group(s) and pyrazolyl group(s) or indolyl groups or both. The mercaptoimidazolyl metal-ligand complex may have formula (I) as shown in FIG. 4 where each instance of $R_1$ and $R_2$ can be hydrogen or a group having one or more carbons. In some embodiments, each instance of $R_1$ and $R_2$ can be hydrogen or an where each instance of $R_1$ and $R_2$ can be hydrogen or a group having one or more carbons. In some embodiments, each instance of $R_1$ and $R_2$ can be hydrogen or an alkyl group having 1 to 5 carbons. L in formula (I) can be a pyrazolyl group, a mercaptoimidazolyl group, or an indolyl. When L is a mercaptoimidazolyl group the multidentate metal-ligand complex can be described as homoleptic. When L is a group other than a mercaptoimidazolyl group the metal ligand complex can be described as a heteroleptic. VOC in formula I is present to show a postulated interaction with the volatile compound having a π bond. Without being bound by theory it is believed that the π bond of the volatile compound coordinates with an empty coordination site on the metal-ligand complex. The coordination alters the electronic configuration of the complex and can impact the electrical properties of the combination of the metal-ligand complex, nanosized particles of a metal dichalcogenide and metallic nanowires. In the case of a metal complex having formula II shown below, the resistivity of the combination of metal-ligand complex, nanosized particles of a metal dichalcogenide and metallic nanowires increases when the metal complex is bound to ethylene.

A more specific example of a mercaptoimidazolyl metal complex is shown in formula (II).

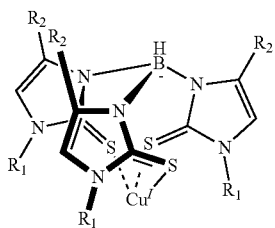

(II)

In formula (II) there are three mercaptoimidazolyl groups. $R_1$ and $R_2$ are defined as in formula (I).

The metal in the mercaptoimidazolyl metal complex may include Group 11 elements such as Cu(I), Ag(I), and Au(I).

Single-walled carbon nanotubes are known materials and are commercially available. Exemplary materials include single-walled nanotubes available from NanoIntegris, US Research Nanomaterials, Inc., Millipore Sigma (formerly Sigma Aldrich), and NanoLab, Inc.

Metallic nanowires are known materials and are commercially available. Nanowires may have a width of 10 nanometers to 1 micrometer and can have a length of 10 micrometers to 1 or more millimeters. Nanowires may have a length to width ratio greater than 1000. The nanowires can comprise one or more elements from Groups 1 12 as well as Al, Ga, In, Sn, Tl, Pb and Bi. In some embodiments the metallic nanowires comprise one or more of Ni, Cu, Au, Pt, or Ag. Methods for nanowire fabrication are described in U.S. Pat. No. 6,843,902.

The nanosized particles of a metal dichalcogenide and single-walled carbon nanotubes or metallic nanowires are applied to a substrate. The substrate may be a flexible polymer film or other suitable material. Exemplary flexible polymer films include polyethylene terephthalate, polyethylene, polypropylene, polyamide, and polyvinyl chloride. The electrodes may be deposited on the substrate before the application of the single-walled carbon nanotubes and nanosized particles of metal chalcogenide. The nanosized particles of a metal chalcogenide and single-walled carbon nanotubes or metallic nanowires may be applied by spray deposition. An example of a formulation that has been used to prepare working sensors is provided as Table 1. These materials are either co-deposited or sequentially deposited. After the nanosized particles of a metal chalcogenide and single-walled carbon nanotubes or metallic nanowires are applied to the substrate the mercaptoimidazolyl metal-ligand complex is deposited on top of the single-walled carbon nanotubes and nanosized particles of a metal dichalcogenide. The mercaptoimidazolyl metal-ligand complex may be applied by drop casting, dip coating, spray coating, or by electrospray. The layered material is then dried and is ready for use.

TABLE 1

| | |
|---|---|
| $H_2O$ | 91 wt % |
| iPrOH | 9 wt % |
| $MoS_2$ | 1.9 ppm |
| SWCNT | 2.5 ppm |
| sodium deoxycholate (surfactant) | <1 wt % |

The sensor may connect to a control module through a direct connection (such as an electrical connection) or wirelessly. The volatile alkene sensing device may further include a suction device, a pressure feeder or both to introduce the gas sample to the volatile alkene sensing device. Use of a suction device, pressure feeder or both allows the volatile alkene sensing device to be attached to the exterior of produce transport container in a removable manner Electricity for the suction device and/or pressure feeder may be provided through the use of a battery or other appropriate means. It is further contemplated that in some embodiments the evaporative fan of a refrigeration unit could be used as the suction device or pressure feeder.

The control module may compare an electrical property value obtained by measuring to a calibration curve to determine the quantity of the volatile alkene present in the sample, A method of sensing a volatile compound having a double or triple bond includes exposing a sensor as described above to a sample and measuring an electrical property at the electrodes. The electrical property can be conductivity or resistivity. The method can also include comparing the obtained electrical property value to a calibration curve to determine the quantity of the volatile compound present in the sample.

The terminology used herein is for the purpose of describing particular embodiments only and is not intended to be limiting of the present disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

While the present disclosure has been described with reference to an exemplary embodiment or embodiments, it will be understood by those skilled in the art that various changes may be made and equivalents may be substituted for elements thereof without departing from the scope of the present disclosure. In addition, many modifications may be made to adapt a particular situation or material to the teachings of the present disclosure without departing from the essential scope thereof. Therefore, it is intended that the present disclosure not be limited to the particular embodiment disclosed as the best mode contemplated for carrying out this present disclosure, but that the present disclosure will include all embodiments falling within the scope of the claims.

What is claimed is:

1. A volatile alkene sensing device comprising a gas pathway having a desiccant area located upstream of a sensor, wherein the sensor is disposed in a housing and the sensor comprises a conductive region in electrical communication with two electrodes and the conductive region comprises nanosized particles of a metal dichalcogenide, a mercaptoimidazolyl metal-ligand complex, and single-walled carbon nanotubes or metallic nanowires.

2. The volatile alkene sensing device of claim 1, wherein the desiccant area comprises a desiccant material.

3. The volatile alkene sensing device of claim 1, wherein the desiccant area is a removable cartridge.

4. The volatile alkene sensing device of claim 1, wherein the sensor is connected to a control module.

5. The volatile alkene sensing device of claim 1, further comprising a suction device, pressure feeder or both.

6. The volatile alkene sensing device of claim 1, wherein the nanosized particles of a metal dichalcogenide comprise $MoS_2$, $WS_2$, $MoSe_2$, $WSe_2$, $MoTe_2$, $WTe_2$, and combinations thereof.

7. The volatile alkene sensing device of claim 1, wherein the mercaptoimidazolyl metal-ligand complex comprises a homoleptic ligand with three mercaptoimidazolyl groups.

8. The volatile alkene sensing device of claim 1, wherein the mercaptoimidazolyl metal-ligand complex comprises Cu(I), Ag(I), or Au(I).

9. The volatile alkene sensing device of claim 1, wherein the mercaptoimidazolyl metal-ligand complex is a homoleptic complex of formula (II):

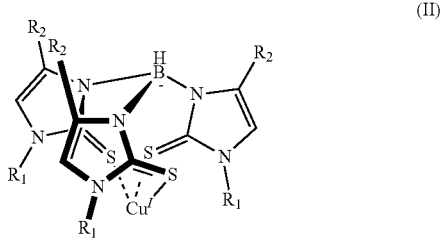

(II)

where each instance of $R_1$ and $R_2$ can be hydrogen, or a group having one or more carbons.

10. A method of sensing a volatile alkene comprising contacting a gaseous sample with a desiccant material to form a treated sample having less than 20% relative humidity, exposing a sensor to the treated sample, and measuring an electrical property of the sensor after exposure to the treated sample, wherein the sensor comprises a conductive region in electrical communication with two electrodes and the conductive region comprises nanosized particles of a metal dichalcogenide, a mercaptoimidazolyl metal-ligand complex and single-walled carbon nanotubes or metallic nanowires.

11. The method of claim 10, wherein the desiccant material comprises $CaSO_4$, $Al_2O_3$, soda lime, and combinations thereof.

12. The method of claim 10, wherein the treated sample has less than 10% relative humidity.

13. The method of claim 10, wherein the electrical property is conductivity.

14. The method of claim 10, wherein the electrical property is resistivity.

15. The method of claim 10, further comprising comparing an electrical property value obtained by measuring to a calibration curve to determine the quantity of a volatile compound having a double or triple bond present in the sample.

16. The method of claim 10, wherein the volatile alkene is ethylene.

17. The method of claim 10, wherein the nanosized particles of a metal dichalcogenide comprise $MoS_2$, $WS_2$, $MoSe_2$, $WSe_2$, $MoTe_2$, $WTe_2$, and combinations thereof.

18. The method of claim 10, wherein the mercaptoimidazolyl metal-ligand complex comprises three mercaptoimidazolyl groups.

19. The method of claim 10, wherein the mercaptoimidazolyl metal-ligand complex comprises Cu(I), Ag(I), or Au(I).

20. The method of claim 10, wherein the mercaptoimidazolyl metal-ligand complex is a complex of formula (II):

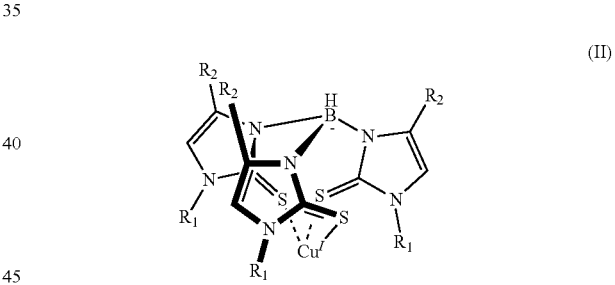

(II)

where each instance of $R_1$ and $R_2$ can be hydrogen, or a group having one or more carbons.

* * * * *